United States Patent
Ji et al.

(10) Patent No.: US 9,635,852 B2
(45) Date of Patent: May 2, 2017

(54) PYMETROZINE SUSPENSION CONCENTRATES AND ITS PREPARATION METHOD

(71) Applicant: Dow Global Technologies LLC, Midland, MI (US)

(72) Inventors: Jing Ji, Shanghai (CN); Ling Zhong, Shanghai (CN); Jianhai Mu, Shanghai (CN)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 15/107,027

(22) PCT Filed: Dec. 23, 2013

(86) PCT No.: PCT/CN2013/090248
§ 371 (c)(1),
(2) Date: Jun. 21, 2016

(87) PCT Pub. No.: WO2015/096013
PCT Pub. Date: Jul. 2, 2015

(65) Prior Publication Data
US 2016/0330953 A1    Nov. 17, 2016

(51) Int. Cl.
| | | |
|---|---|---|
| *A01N 43/64* | (2006.01) | |
| *A01N 25/04* | (2006.01) | |
| *A01N 43/707* | (2006.01) | |
| *C08L 35/00* | (2006.01) | |
| *A01N 31/14* | (2006.01) | |

(52) U.S. Cl.
CPC .............. *A01N 25/04* (2013.01); *A01N 31/14* (2013.01); *A01N 43/707* (2013.01); *C08L 35/00* (2013.01)

(58) Field of Classification Search
CPC ..................................................... A61K 31/53
USPC ......................................................... 514/242
See application file for complete search history.

(56) References Cited

U.S. PATENT DOCUMENTS

| | | | |
|---|---|---|---|
| 3,646,099 | A | 2/1972 | Dannals |
| 4,301,266 | A | 11/1981 | Muenster et al. |
| 4,314,004 | A | 2/1982 | Stoneberg |
| 4,663,364 | A | 5/1987 | Iwasaki et al. |
| 4,711,725 | A | 12/1987 | Amick et al. |
| 4,851,421 | A | 7/1989 | Iwasaki et al. |
| 4,931,439 | A | 6/1990 | Kristinsson |
| 5,854,197 | A | 12/1998 | Duccini et al. |
| 8,247,353 | B2 | 8/2012 | Stern et al. |
| 2002/0099053 | A1 | 7/2002 | Gutmann |

FOREIGN PATENT DOCUMENTS

| | | |
|---|---|---|
| CN | 103030730 | 4/2013 |
| EP | 0357149 | 3/1992 |
| WO | 2013020937 | 2/2013 |

OTHER PUBLICATIONS

International Search Report and Written Opinion for related PCT Application PCT/CN2013/090248, mailed Sep. 26, 2014 (12 pgs).

*Primary Examiner* — Raymond Henley, III
(74) *Attorney, Agent, or Firm* — Brooks, Cameron & Huebsch, PLLC (57) ABSTRACT

The present disclosure relates generally to insecticide formulations. The present disclosure relates more particularly to aqueous pymetrozine formulations that can be provided in concentrate form and methods for making them. In one aspect, the disclosure provides a composition including pymetrozine in particulate form; a first polymeric dispersing agent, the first polymeric dispersing agent being a copolymer of (a) a maleic acid monomer and (b) a hydrophobic monomer; and a second polymeric dispersing agent, the second polymeric dispersing agent being a copolymer of (a) a (meth)acrylic acid monomer, an ethylenically unsaturated dicarboxylic acid monomer or a combination thereof, (b) a (meth)acrylamido alkyl or aryl sulfonate monomer; and (c) a third monomer selected from one or more of vinylic compounds, (meth)acrylic esters, vinyl acetate, and substituted (meth)acrylamides.

15 Claims, 1 Drawing Sheet

PYMETROZINE SUSPENSION CONCENTRATES AND ITS PREPARATION METHOD

This application is a National Stage Application under 35 U.S.C. §371 of International Application Number PCT/CN2013/090248, filed Dec. 23, 2013 and published as WO 2015/096013 on Jul. 2, 2015, the entire contents of which are incorporated herein by reference in its entirety.

BACKGROUND OF THE INVENTION

Field of the Invention

The present disclosure relates generally to insecticide formulations. The present disclosure relates more particularly to aqueous pymetrozine formulations that can be provided in concentrate form and methods for making them.

Technical Background

Pymetrozine is an azomethine insecticide commonly used in integrated crop management to control aphids, whiteflies and other pests. It is plant-systemic and readily taken up by leaves and roots and translocated throughout the plant. Plants are immediately protected upon application because insect feeding stops soon after ingestion of pymetrozine. While pymetrozine is generally considered safe for use on food crops, there is evidence of carcinogenic effects at high doses.

The conventional formulation of pymetrozine is as a so-called "wettable powder," in which the pymetrozine is provided in a finely ground state combined with wetting agents and sometimes bulking agents. For application to plants, the wettable powder is dispersed in a large quantity of water and sprayed over a field. Wettable powders can be advantageous in that the pymetrozine can be provided in concentrated form and thus the weight and volume of a dilute pymetrozine suspension need not be managed until the point of use. However, wettable powders have a serious disadvantage: they can be rather dusty, and can create dust pollution and an acute inhalation hazard to operators (especially problematic given the potential carcinogenicity of pymetrozine).

Water-based formulations are considered much more environmentally benign and safe, as they produce no dust and include little or no aromatic solvent. Microparticulate pymetrozine can be suspended in water at relatively high concentrations to produce a suspension concentrate. Suspension concentrates can overcome the problems with dust of wettable powders, and can provide a number of additional advantages, such as ease of pouring and measuring. However, it can be difficult to prepare suspension concentrate formulations that are storage stable, e.g., with respect to thickening and particle agglomeration, especially for active ingredients having high water solubility such as pymetrozine.

There remains a need for pymetrozine formulations that can address these shortcomings.

SUMMARY OF THE INVENTION

In certain aspects, the present invention addresses the need for a stable, concentrated, dust-free pymetrozine formulation suitable for dilution in water and application to plants.

In one aspect, the disclosure provides a composition including pymetrozine in particulate form;
a first polymeric dispersing agent, the first polymeric dispersing agent being a copolymer comprising as polymerized units (a) from about 20 to about 90 weight percent, based on total polymer weight, of a maleic acid monomer selected from one or more of maleic acid, maleic anhydride and water-soluble salts thereof, and (b) from about 10 to about 80 weight percent, based on total polymer weight, of a hydrophobic monomer selected from one or more of alkenes, dienes, alkynes and aromatic compounds, each containing from 4 to 20 carbon atoms; and
a second polymeric dispersing agent, the second polymeric dispersing agent being a copolymer copolymer comprising as polymerized units (a) from about 10 to about 84 weight percent, based on total polymer weight, of a (meth)acrylic acid monomer selected from one or more of (meth)acrylic acid and salts thereof, an ethylenically unsaturated dicarboxylic acid monomer or a combination thereof, (b) from about 11 to about 40 weight percent, based on total polymer weight, of a (meth)acrylamido alkyl or aryl sulfonate monomer; and (c) from about 5 to about 50 weight percent based on total polymer weight, of a third monomer selected from one or more of vinylic compounds, (meth)acrylic esters, vinyl acetate, and substituted (meth)acrylamides.

In another aspect, the disclosure provides a method for making a composition as described herein, the method including
providing a first polymeric dispersing agent as described herein;
providing a second polymeric dispersing agent as described herein;
mixing the first polymeric dispersing agent and the second polymeric dispersing agent and water with particulate pymetrozine with high-speed shearing; and
grinding the resulting mixture.

In another aspect, the disclosure provides a method for reducing insect populations on a plant, the method comprising
diluting a composition as described herein with water to provide a diluted pymetrozine composition; and
contacting the plant with the diluted pymetrozine concentration.

The present invention is capable of providing a number of advantages over the prior art. For example, in certain embodiments the compositions described herein can be provided as concentrated aqueous liquids that do not expose the user to dust, for example, when diluting the concentrated liquid for use. Thus, in certain embodiments the compositions described herein can be safer for use than conventional wettable powders. In certain embodiments, the compositions described herein are storage stable, especially with respect to viscosity and particle size, even at high concentrations of pymetrozine. As liquid formulations can be prepared, in certain embodiments the compositions described herein can be more ecologically-friendly than organic solvent-containing formulations. Moreover, in certain embodiments the invention provides a simplified method of making a pymetrozine-containing composition; use of the polymeric dispersing agents described herein can allow dry-form pymetrozine to be mixed directly with water, without requiring a wetting step. Additional features and advantages of the invention will be set forth in the detailed description which follows and will be readily apparent to those skilled in the art from the description or recognized by practicing the invention as described in the written description and claims hereof, as well as in the appended drawings.

It is to be understood that both the foregoing general description and the following detailed description are merely exemplary of the invention, and are intended to provide an overview or framework for understanding the nature and character of the invention as it is claimed.

DETAILED DESCRIPTION OF THE INVENTION

Figure 1:
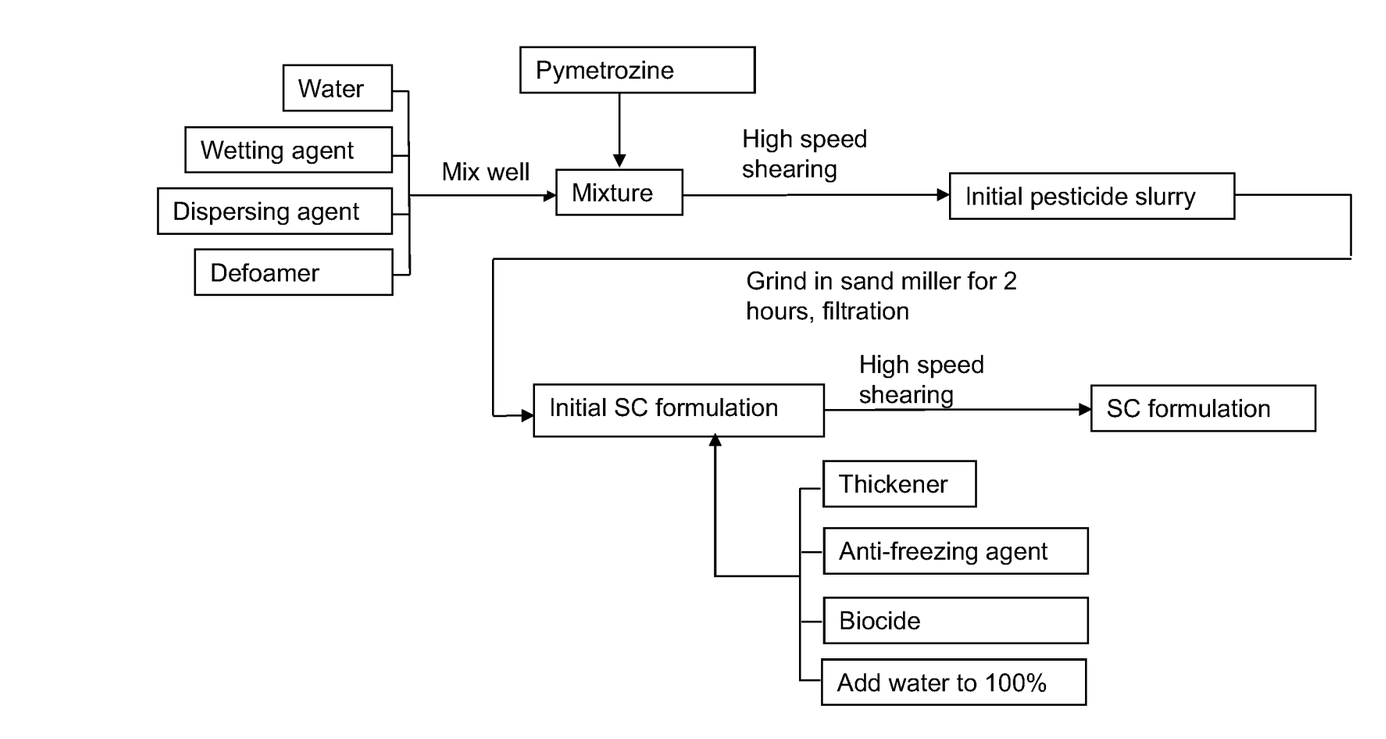
The FIGURE is a flowchart depicting a method for making a pymetrozine composition according to one embodiment of the invention.

One embodiment of the invention is a composition including pymetrozine in particulate form;
a first polymeric dispersing agent, the first polymeric dispersing agent being a copolymer comprising as polymerized units (a) from about 20 to about 90 weight percent, based on total polymer weight, of a maleic acid monomer selected from one or more of maleic acid, maleic anhydride and water-soluble salts thereof, and (b) from about 10 to about 80 weight percent, based on total polymer weight, of a hydrophobic monomer selected from one or more of alkenes, dienes, alkynes and aromatic compounds, each containing from 4 to 20 carbon atoms; and
a second polymeric dispersing agent, the second polymeric dispersing agent being a copolymer comprising as polymerized units (a) from about 10 to about 84 weight percent, based on total polymer weight, of a (meth)acrylic acid monomer selected from one or more of (meth)acrylic acid and salts thereof, an ethylenically unsaturated dicarboxylic acid monomer or a combination thereof, (b) from about 11 to about 40 weight percent, based on total polymer weight, of an (meth) acrylamido alkyl or aryl sulfonate monomer; and (c) from about 5 to about 50 weight percent based on total polymer weight, of a third monomer selected from one or more of vinylic compounds, (meth)acrylic esters, vinyl acetate, and substituted (meth)acrylamides.

In certain embodiments, the second polymeric dispersing agent is a copolymer comprising as polymerized units (a) from about 10 to about 84 weight percent, based on total polymer weight, of a (meth)acrylic acid monomer selected from one or more of (meth)acrylic acid and salts thereof, (b) from about 11 to about 40 weight percent, based on total polymer weight, of a (meth)acrylamido alkyl or aryl sulfonate monomer; and (c) from about 5 to about 50 weight percent based on total polymer weight, of a third monomer selected from one or more of vinylic compounds, (meth) acrylic esters, vinyl acetate, and substituted (meth)acrylamides.

Pymetrozine (4,5-dihydro-6-methyl-4-[(E)-(3-pyridinylmethylene)amino]-1,2,4-triazin-3(2H)-one) is a member of the pyridine azomethine family of pesticides disclosed in U.S. Pat. No. 4,931,439, which is hereby incorporated herein by reference in its entirety. Pymetrozine has the structural formula:

As the person of ordinary skill in the art will appreciate, the pymetrozine can be provided in a variety of forms. For example, the pymetrozine can be provided in any desired agrochemically acceptable amorphous or crystalline form. The pymetrozine can be provided, for example, as a salt or as a solvate. Solvates of pymetrozine are disclosed in U.S. Patent Application Publication no. 2002/0099053, which is hereby incorporated herein by reference in its entirety.

The pymetrozine is present in particulate form in compositions described herein according to various embodiments of the invention. In certain embodiments of the compositions as described herein, the pymetrozine has a mean particle size within the range of about 0.1 to about 10 µm, for example, within the range of about 0.5 to about 5 µm or within the range of about 0.5 to about 5 µm; a median particle size within the range of about 0.1 to about 10 µm, for example, within the range of about 0.5 to about 5 µm or within the range of about 0.5 to about 5 µm; or a mean particle size and a median particle size each within the range of about 0.1 to about 10 µm, for example, within the range of about 0.5 to about 5 µm or within the range of about 0.5 to about 5 µm. In certain embodiments of the compositions as described herein, the pymetrozine has a $D_{90}$ no greater than about 10 µm, or even no greater than about 5 µm. The pymetrozine is desirably provided in a solid form. The solid pymetrozine used to make the concentrated formulations described herein can be provided with any convenient particle size; as described in more detail below, a grinding step can be used to reduce the pymetrozine particle size to a desired particle size (e.g., mean particle size within the range of about 0.5 to about 5 µm, or as otherwise described above).

The first polymeric dispersing agent is a copolymer comprising as polymerized units from about 20 to about 90 weight percent, based on total polymer weight, of a maleic acid monomer selected from one or more of maleic acid, maleic anhydride and water-soluble salts thereof, and from about 10 to about 80 weight percent, based on total polymer weight, of a hydrophobic monomer selected from one or more of alkenes, dienes, alkynes and aromatic compounds, each containing from 4 to 20 carbon atoms. Such polymers are described in U.S. Pat. No. 5,854,197, which is hereby incorporated herein by reference in its entirety. In certain embodiments, the first polymeric dispersing agent is a copolymer comprising as polymerized units of maleic acid monomer from about 30 to about 60 weight percent and the polymerized units of hydrophobic monomer from about 40 to about 70 weight percent, based on total polymer weight. In certain embodiments, the hydrophobic monomer is selected from one or more of alkenes, dienes, alkynes and aromatic compounds, each containing from 6 to 10 carbon atoms. In certain embodiments, the hydrophobic monomer is one or more of isobutylene, diisobutylene, styrene, decene, limonene, linalool and eicosene. In certain embodiments, for example, the hydrophobic monomer is one or more of diisobutylene, styrene, linalool and limonene. In one embodiment, the hydrophobic monomer is diisobutylene. In one embodiment as otherwise described herein, the hydrophobic monomer is selected from one or more of alkenes, dienes and alkynes.

As described herein, many of the monomers described herein can be provided as anhydrides or as salts. For purposes of weight percent calculations, all carboxylic acid monomers and anhydrides and salts thereof are calculated as the parent carboxylic acids. Accordingly, all salts and anhydrides of maleic acid are to be calculated for weight percent purposes as maleic acid, and all salts of acrylic acid are calculated for weight percent purposes as acrylic acid. Similarly, all salts of sulfonic acids are calculated for weight percent purposes as the parent sulfonic acid. For example, all salts of 2-acrylamido-2-methylpropanesulfonic acid are calculated for weight percent purposes as 2-acrylamido-2-methylpropanesulfonic acid.

In certain embodiments, the first polymeric dispersing agent includes no other monomers, i.e., it is a copolymer only of the maleic acid monomer and the hydrophobic monomer. For example, in one embodiment, the first polymeric dispersing agent is a copolymer only of the maleic acid monomer and one or more of diisobutylene, styrene, linalool and limonene. In one embodiment, the first polymeric dispersing agent is a copolymer only of the maleic acid monomer and diisobutylene. In other embodiments, however, a minor amount of polymerized units of other monomers may be included. For example, up to 1 weight percent, up to 2 weight percent, up to 5 weight percent, up to 10 weight percent or even up to 20 weight percent of one or more additional monomers may be included.

Particular examples of first polymeric dispersing agents include, for example: about 45 to about 55 weight percent (e.g., about 50 weight percent) maleic acid monomer (e.g., maleic acid) and about 45 to about 55 weight percent (e.g., about 50 weight percent) diisobutylene; about 46 to about 56 weight percent (e.g., about 51 weight percent) maleic acid monomer (e.g., maleic acid) and about 44 to about 54 weight percent (e.g., about 49 weight percent) diisobutylene; about 44 to about 54 weight percent (e.g., about 49 weight percent) maleic acid monomer (e.g., maleic acid) and about 46 to about 56 weight percent (e.g., about 51 weight percent) diisobutylene; about 35 to about 54 weight percent (e.g., about 40 weight percent) maleic acid monomer (e.g., maleic acid) and about 55 to about 65 weight percent (e.g., about 60 weight percent) limonene; about 32 to about 42 weight percent (e.g., about 37 weight percent) maleic acid monomer (e.g., maleic acid) and about 58 to about 68 weight percent (e.g., about 63 weight percent) linalool; about 37 to about 47 weight percent (e.g., about 42 weight percent) maleic acid monomer (e.g., maleic acid), about 24 to about 34 weight percent (e.g., about 29 weight percent) diisobutylene and about 24 to about 34 weight percent (e.g., about 29 weight percent) limonene; about 38 to about 48 weight percent (e.g., about 43 weight percent) maleic acid monomer (e.g., maleic acid), about 36 to about 46 weight percent (e.g., about 41 weight percent) diisobutylene and about 11 to about 21 weight percent (e.g., about 16 weight percent) limonene; and about 85 to about 95 weight percent (e.g., about 90 weight percent) maleic acid monomer (e.g., maleic acid) and about 5 to about 15 weight percent (e.g., about 10 weight percent) styrene.

In certain embodiments of the compositions as described herein, the first polymeric dispersing agent has a weight-average molecular weight within the range of about 1 kDa to about 20 kDa, for example, within the range of about 10 kDa to about 20 kDa. The first polymeric dispersing agent can be made using procedures familiar to the person of ordinary skill in the art.

The second polymeric dispersing agent is a copolymer comprising as polymerized units from about 10 to about 84 weight percent, based on total polymer weight, of a (meth)acrylic acid monomer selected from one or more of (meth)acrylic acid and salts thereof, from about 11 to about 40 weight percent, based on total polymer weight, of a (meth)acrylamido alkyl or aryl sulfonate monomer; and about 5 to about 50 weight percent based on total polymer weight, of a third monomer selected from one or more of vinylic compounds, (meth)acrylic esters, vinyl acetate, and substituted (meth)acrylamides. Such polymers are described in U.S. Pat. No. 4,711,725, which is hereby incorporated herein by reference in its entirety.

The (meth)acrylic acid monomer is represented by the structural formula $CH_2=C(R^1)-COOX$, in which $R^1$ is H or $CH_3$ and X is hydrogen, a metal cation or $N(R^2)_4$ in which each $R^2$ is independently H, $C_1$-$C_4$ alkyl or $C_1$-$C_4$ hydroxyalkyl. In certain embodiments, $R^1$ is H, i.e., the (meth)acrylic acid monomer is an acrylic acid monomer, such as acrylic acid or a sodium salt thereof. In other embodiments, $R^1$ is $CH_3$, i.e., the (meth)acrylic acid monomer is a methacrylic acid monomer, such as methacrylic acid or a sodium salt thereof. In certain embodiments as described herein (e.g., when $R^1$ is H or $CH_3$), X is H. In other embodiments, X is a metal cation (e.g., sodium). In certain embodiments, the second polymeric dispersing agent includes at least about 30 weight percent by weight of the (meth)acrylic acid monomer.

In certain embodiments of the compositions as described herein, an ethylenically unsaturated dicarboxylic acid monomer (i.e., in diacid form, or as an anhydride or salt thereof) can be used in place of part or all of the (meth)acrylic acid monomer. For example, maleic acid, fumaric acid, itaconic acid, or an anhydride or salt thereof can be used in place of part or all of the (meth)acrylic acid monomer. The weight percents described below with respect to the (meth)acrylic acid monomer can be used for the ethylenically unsaturated dicarboxylic acid monomer or for a combination of the (meth)acrylic acid monomer and the ethylenically unsaturated dicarboxylic acid monomer. But in other embodiments of the compositions as described herein, no ethylenically unsaturated dicarboxylic acid monomer is used in place of part or all of the (meth)acrylic acid monomer.

The (meth)acrylamido alkyl or aryl sulfonate monomer is represented by the formula $CH_2=C(R^3)-C(O)N(R^4)-R^5-SO_3X$, in which $R^3$ is H or $CH_3$, $R^4$ is H or $C_1$-$C_4$ alkyl, $R^5$ is $C_1$-$C_8$ alkylene (i.e., straight chain or branched) or $C_8$-$C_1^o$ alkarylene; and X is as described above. For example, in certain embodiments as described herein, $R^3$ is H. In other embodiments, $R^3$ is CH3. In certain embodiments as described herein, R4 is H. In certain embodiments as described herein, $R^5$ is $C_2$-$C_6$ alkyl, e.g., $-C(CH_3)_2-CH_2-$. In certain embodiments as described herein, X is H. In other embodiments, X is a metal ion (e.g., sodium). In certain embodiments, the (meth)acrylamido alkyl or aryl sulfonate monomer is 2-acrylamido-2-methylpropanesulfonic acid (AMPS). In certain embodiments, the second polymeric dispersing agent includes from about 5 to about 30 weight percent of the acrylamide alkyl or aryl sulfonate monomer.

As described above, the third monomer can be one or more of vinylic compounds, (meth)acrylic esters, vinyl acetate, and substituted acrylamides. The vinylic compounds are vinyl alcohols or vinyl ethers and are represented by the formula $CH_2=C(R^8)-O-(CH_2-CH(R^8)-O)_n-R^9$ in which $R^8$ is H or $CH_3$, $R^9$ is H or $C_1$-$C_6$ alkyl and n is 0, 1 or 2. In certain embodiments as described herein, $R^8$ is H. In other embodiments, $R^8$ is $CH_3$. In certain embodiments as described herein, $R^9$ is H. In other embodiments, $R^9$ is $C_1$-$C_3$ alkyl. The substituted (meth)acrylates are represented by the formula $CH_2=C(R^6)-C(O)OR^7$ in which $R^6$ is H or $CH_3$ and $R^7$ is $C_1$-$C_6$ alkyl, $C_1$-$C_6$ hydroxalkyl, ($C_1$-$C_6$ alkoxy)$C_1$-$C_6$ alkyl, $C_6$-$C_{10}$ aryl or $C_6$-$C_{10}$ aralkyl. In certain embodiments as described herein, $R^6$ is H. In other embodiments, $R^6$ is $CH_3$. In certain embodiments as described herein, $R^7$ is $C_1$-$C_4$ alkyl (e.g., ethyl). In other embodiments, R⁷ is $C_1$-$C_4$ hydroxylalkyl (e.g., 2-hydroxyethyl, 3-hydroxypropyl, or 2-hydroxybutyl. In certain embodiments, the (meth)acrylic ester is one or more of ethyl acrylate, hydroxyethyl methacrylate, hydroxypropyl acrylate and cellosolve acrylate. The substituted (meth)acrylamides are represented by the formula $CH_2\!\!=\!\!C(R^{10})\!\!-\!\!C(O)NR^{11}R^{12}$, in which $R^{10}$ is H or $CH_3$ and $R^{11}$ and $R^{12}$ are independently H, $C_1$-$C_8$ alkyl, $C_6$-$C_8$ cycloalkyl, benzyl or —$(CH_2$—$CH(R^8)$—$O)_m$—$R^9$ in which m is 1, 2 or 3 and $R^8$ and $R^9$ are as described above, provided that at least one of $R^{11}$ and $R^{12}$ is not H. In certain embodiments, each of $R^{11}$ and $R^{12}$ is H or $C_1$-$C_8$ alkyl, provided that at least one is $C_1$-$C_8$ alkyl. In certain embodiments as described herein, $R^{10}$ is H. In other embodiments, $R^{10}$ is $CH_3$. In certain embodiments as described herein, $R^{11}$ is H and $R^{12}$ is $C_1$-$C_8$ alkyl (e.g., t-butyl). In certain embodiments as described herein, the substituted (meth)acrylamide is one or more of t-butyl acrylamide, t-octyl acrylamide, dimethyl acrylamide, ethyl acrylamide, propyl acrylamide, cyclohexyl methacrylamide, t-butyl methacrylamide and benzyl methacrylamide. For example, in one embodiment, the substituted (meth)acrylamide is one or more of t-butyl acrylamide, t-octyl acrylamide and dimethyl acrylamide. For example, in one particular embodiment, the substituted (meth)acrylamide is t-butyl acrylamide. In certain embodiments, the third monomer is a substituted acrylamide. In certain embodiments, the second polymeric dispersing agent includes from about 5 to about 30 weight percent by weight of the third monomer.

In certain embodiments of the second dispersing agents as described herein, the second dispersing agent has a weight average molecular weight ranging from about 3 to about 25 kDa, for example, from about 4 to about 8 kDa.

In certain embodiments, the second polymeric dispersing agent includes no other monomers, i.e., it is a copolymer only of the (meth)acrylic acid monomer, the (meth)acrylamido alkyl or aryl sulfonate monomer and the third monomer as described above. For example, in one embodiment, the second polymeric dispersing agent is a copolymer only of acrylic acid (or, in other embodiments, methacrylic acid) or a salt thereof; AMPS or a salt thereof; and a third monomer selected from one or more of ethyl acrylate, tert-butyl acrylate, vinyl acetate, hydroxyethyl methacrylate, hydroxypropyl acrylate, dimethyl acrylamide, ethyl acrylamide, propyl acrylamide, t-butyl acrylamide, t-octyl acrylamide, cyclohexyl methacrylamide, t-butyl metacrylamide, benzyl methacrylamide, cellosolve acrylate. In one embodiment, the first polymeric dispersing agent is a copolymer only of the acrylic acid (or methacrylic acid), AMPS, and an alkyl-substituted (meth)acrylamide monomer and diisobutylene. In other embodiments, however, a minor amount of polymerized units of other monomers may be included. For example, up to 1 weight percent, up to 2 weight percent, up to 5 weight percent, up to 10 weight percent or even up to 20 weight percent of one or more additional monomers may be included.

In certain embodiments, the second polymeric dispersing agent includes no other monomers, i.e., it is a copolymer only of the (meth)acrylic acid monomer, the ethylenically unsaturated dicarboxylic acid monomer or the combination of the ethylenically unsaturated dicarboxylic acid monomer and the (meth)acrylic acid monomer, the (meth)acrylamido alkyl or aryl sulfonate monomer and the third monomer as described above. In other embodiments, however, a minor amount of polymerized units of other monomers may be included. For example, up to 1 weight percent, up to 2 weight percent, up to 5 weight percent, up to 10 weight percent or even up to 20 weight percent of one or more additional monomers may be included.

In certain embodiments, the second polymeric dispersing agent is a copolymer of about 67 to about 77 weight percent (e.g., about 72 weight percent) (meth)acrylic acid monomer (e.g., acrylic acid), about 18 to about 28 weight percent (e.g., about 23 weight percent) (meth)acrylamido alkyl or aryl sulfonate monomer (e.g., AMPS) and about 5 to about 10 weight percent (e.g., about 5 weight percent) third monomer (e.g., ethyl acrylate); about 61 to about 68 weight percent (e.g., about 64.5 weight percent) (meth)acrylic acid monomer (e.g., t-butyl acrylamide), about 23 to about 31 weight percent (e.g., about 27 weight percent) (meth)acrylamido alkyl or aryl sulfonate monomer (e.g., AMPS) and about 5 to about 12 weight percent (e.g., about 8.5 weight percent) third monomer (e.g., t-butyl acrylamide); about 59 to about 70 weight percent (e.g., about 64.5 weight percent) (meth)acrylic acid monomer (e.g., t-butyl acrylamide), about 21 to about 22 weight percent (e.g., about 27 weight percent) (meth)acrylamido alkyl or aryl sulfonate monomer (e.g., AMPS) and about 5 to about 14 weight percent (e.g., about 8.5 weight percent) third monomer (e.g., t-butyl acrylamide); about 57 to about weight percent (e.g., about 62 weight percent (meth)acrylic acid monomer (e.g., acrylic acid), about 18 weight percent to about 28 weight percent (e.g., about 23 weight percent) (meth)acrylamido alkyl or aryl sulfonate monomer (e.g., AMPS) and about 10 to about 20 weight percent (e.g., about 15 weight percent) third monomer (e.g., t-butyl acrylamide); about 62 to about 72 weight percent (e.g., about 67 weight percent) (meth)acrylic acid monomer (e.g., acrylic acid), about 18 to about 28 weight percent (e.g., about 23 weight percent) (meth)acrylamido alkyl or aryl sulfonate monomer (e.g., AMPS) and about 5 to about 15 weight percent (e.g., about 10 weight percent) third monomer (e.g., ethyl acrylate); about 52 to about 62 weight percent (e.g., about 57 weight percent) (meth)acrylic acid monomer (e.g., acrylic acid), about 18 to about 28 weight percent (e.g., about 23 weight percent) (meth)acrylamido alkyl or aryl sulfonate monomer (e.g., AMPS) and about 15 to about 25 weight percent (e.g., about 20 weight percent) third monomer (e.g., ethyl acrylate); about 62 to about 72 weight percent (e.g., about 67 weight percent) (meth)acrylic acid monomer (e.g., acrylic acid), about 18 to about 28 weight percent (e.g., about 23 weight percent) (meth)acrylamido alkyl or aryl sulfonate monomer (e.g., AMPS) and about 5 to about 15 weight percent (e.g., about 10 weight percent) third monomer (e.g., t-butyl acrylate); about 52 to about 62 weight percent (e.g., about 57 weight percent) (meth)acrylic acid monomer (e.g., acrylic acid), about 18 to about 28 weight percent (e.g., about 23 weight percent) (meth)acrylamido alkyl or aryl sulfonate monomer (e.g., AMPS) and about 15 to about 25 weight percent (e.g., about 20 weight percent) third monomer (e.g., vinyl acetate); about 64 to about 74 weight percent (e.g., about 69 weight percent) (meth)acrylic acid monomer (e.g., acrylic acid), about 11 to about 16 weight percent (e.g., about 11 weight percent) (meth)acrylamido alkyl or aryl sulfonate monomer (e.g., AMPS) and about 15 to about 25 weight percent (e.g., about 20 weight percent) third monomer (e.g., hydroxyethyl methacrylate); about 58 to about 68 weight percent (e.g., about 63 weight percent) (meth)acrylic acid monomer (e.g., acrylic acid), about 12 to about 22 weight percent (e.g., about 17 weight percent) (meth)acrylamido alkyl or aryl sulfonate monomer (e.g., AMPS) and about 15 to about 25 weight percent (e.g., about 20 weight percent) third monomer (e.g., hydroxyethyl methacrylate); about 67 to about 77 weight percent (e.g., about 72 weight percent)

(meth)acrylic acid monomer (e.g., acrylic acid), about 18 to about 28 weight percent (e.g., about 23 weight percent) (meth)acrylamido alkyl or aryl sulfonate monomer (e.g., AMPS) and about 5 to about 10 weight percent (e.g., about 5 weight percent) third monomer (e.g., hydroxyethyl methacrylate); about 62 to about 72 weight percent (e.g., about 67 weight percent) (meth)acrylic acid monomer (e.g., acrylic acid), about 18 to about 28 weight percent (e.g., about 23 weight percent) (meth)acrylamido alkyl or aryl sulfonate monomer (e.g., AMPS) and about 5 to about 15 weight percent (e.g., about 10 weight percent) third monomer (e.g., hydroxyethyl methacrylate); about 52 to about 62 weight percent (e.g., about 57 weight percent) (meth)acrylic acid monomer (e.g., acrylic acid), about 18 to about 28 weight percent (e.g., about 23 weight percent) (meth)acrylamido alkyl or aryl sulfonate monomer (e.g., AMPS) and about 15 to about 25 weight percent (e.g., about 20 weight percent) third monomer (e.g., hydroxyethyl methacrylate); about 42 to about 52 weight percent (e.g., about 47 weight percent) (meth)acrylic acid monomer (e.g., acrylic acid), about 18 to about 28 weight percent (e.g., about 23 weight percent) (meth)acrylamido alkyl or aryl sulfonate monomer (e.g., AMPS) and about 25 to about 35 weight percent (e.g., about 30 weight percent) third monomer (e.g., hydroxyethyl methacrylate); about 58 to about 68 weight percent (e.g., about 63 weight percent) (meth)acrylic acid monomer (e.g., acrylic acid), about 12 to about 22 weight percent (e.g., about 17 weight percent) (meth)acrylamido alkyl or aryl sulfonate monomer (e.g., AMPS) and about 15 to about 25 weight percent (e.g., about 20 weight percent) third monomer (e.g., hydroxypropyl acrylate); about 67 to about 77 weight percent (e.g., about 72 weight percent) (meth)acrylic acid monomer (e.g., acrylic acid), about 18 to about 28 weight percent (e.g., about 23 weight percent) (meth)acrylamido alkyl or aryl sulfonate monomer (e.g., AMPS) and about 5 to about 10 weight percent (e.g., about 5 weight percent) third monomer (e.g., hydroxypropyl acrylate); about 62 to about 72 weight percent (e.g., about 67 weight percent) (meth)acrylic acid monomer (e.g., acrylic acid), about 18 to about 28 weight percent (e.g., about 23 weight percent) (meth)acrylamido alkyl or aryl sulfonate monomer (e.g., AMPS) and about 5 to about 15 weight percent (e.g., about 10 weight percent) third monomer (e.g., hydroxypropyl acrylate); about 52 to about 62 weight percent (e.g., about 57 weight percent) (meth)acrylic acid monomer (e.g., acrylic acid), about 18 to about 28 weight percent (e.g., about 23 weight percent) (meth)acrylamido alkyl or aryl sulfonate monomer (e.g., AMPS) and about 15 to about 25 weight percent (e.g., about 20 weight percent) third monomer (e.g., hydroxypropyl acrylate); about 42 to about 52 weight percent (e.g., about 47 weight percent) (meth)acrylic acid monomer (e.g., acrylic acid), about 18 to about 28 weight percent (e.g., about 23 weight percent) (meth)acrylamido alkyl or aryl sulfonate monomer (e.g., AMPS) and about 25 to about 35 weight percent (e.g., about 30 weight percent) third monomer (e.g., hydroxypropyl acrylate); about 67 to about 77 weight percent (e.g., about 72 weight percent) (meth)acrylic acid monomer (e.g., acrylic acid), about 18 to about 28 weight percent (e.g., about 23 weight percent) (meth)acrylamido alkyl or aryl sulfonate monomer (e.g., AMPS) and about 5 to about 10 weight percent (e.g., about 5 weight percent) third monomer (e.g., dimethylacrylamide); about 62 to about 72 weight percent (e.g., about 67 weight percent) (meth)acrylic acid monomer (e.g., acrylic acid), about 18 to about 28 weight percent (e.g., about 23 weight percent) (meth)acrylamido alkyl or aryl sulfonate monomer (e.g., AMPS) and about 5 to about 15 weight percent (e.g., about 10 weight percent) third monomer (e.g., dimethylacrylamide); about 52 to about 62 weight percent (e.g., about 57 weight percent) (meth)acrylic acid monomer (e.g., acrylic acid), about 18 to about 28 weight percent (e.g., about 23 weight percent) (meth)acrylamido alkyl or aryl sulfonate monomer (e.g., AMPS) and about 15 to about 25 weight percent (e.g., about 20 weight percent) third monomer (e.g., dimethyl acrylamide, ethyl acrylamide, propyl acrylamide, cyclohexylmethylacrylamide, t-butyl methacrylamide, benzyl methacrylamide or cellosolve acrylate); about 62 to about 72 weight percent (e.g., about 67 weight percent) (meth)acrylic acid monomer (e.g., acrylic acid), about 18 to about 28 weight percent (e.g., about 23 weight percent) (meth)acrylamido alkyl or aryl sulfonate monomer (e.g., AMPS) and about 5 to about 15 weight percent (e.g., about 10 weight percent) third monomer (e.g., t-butyl acrylamide); about 52 to about 62 weight percent (e.g., about 57 weight percent) (meth)acrylic acid monomer (e.g., acrylic acid), about 18 to about 28 weight percent (e.g., about 23 weight percent) (meth)acrylamido alkyl or aryl sulfonate monomer (e.g., AMPS) and about 15 to about 25 weight percent (e.g., about 20 weight percent) third monomer (e.g., t-butyl acrylamide); about 62 to about 72 weight percent (e.g., about 67 weight percent) (meth)acrylic acid monomer (e.g., acrylic acid), about 18 to about 28 weight percent (e.g., about 23 weight percent) (meth)acrylamido alkyl or aryl sulfonate monomer (e.g., AMPS) and about 5 to about 15 weight percent (e.g., about 10 weight percent) third monomer (e.g., t-octyl acrylamide, cyclohexylmethylacrylamide or cellosolve acrylate); or about 52 to about 62 weight percent (e.g., about 57 weight percent) (meth)acrylic acid monomer (e.g., acrylic acid), about 18 to about 28 weight percent (e.g., about 23 weight percent) (meth)acrylamido alkyl or aryl sulfonate monomer (e.g., AMPS) and about 15 to about 25 weight percent (e.g., about 20 weight percent) third monomer (e.g., 10% each of hydroxyethyl methacrylate and t-butyl acrylamide; or 10% each of ethyl acrylate and t-butyl acrylamide).

Any and all combinations of the particular first polymeric dispersing agents and second polymeric dispersing agents described herein are specifically contemplated. For example, in one particular embodiment, the first polymeric dispersing agent is a copolymer of about 46 to about 56 weight percent (e.g., about 51 weight percent) maleic acid monomer (e.g., maleic acid) and about 44 to about 54 weight percent (e.g., about 49 weight percent) diisobutylene; and the second polymeric dispersing agent is a copolymer of about 61 to about 68 weight percent (e.g., about 64.5 weight percent) (meth)acrylic acid monomer (e.g., acrylic acid), about 23 to about 31 weight percent (e.g., about 27 weight percent) (meth)acrylamido alkyl or aryl sulfonate monomer (e.g., AMPS) and about 5 to about 12 weight percent (e.g., about 8.5 weight percent) third monomer (e.g., t-butyl acrylamide).

In the above-described embodiments, the various monomers can optionally be provided in salt form. However, as described above, in such cases, the weight percent amounts of such salt form monomers are calculated as the carboxylic acid or dicarboxylic acid.

In certain embodiments, the second polymeric dispersing agent is a copolymer comprising, as polymerized units, about 61 to about 68 weight percent (e.g., about 64.5 weight percent) (meth)acrylic acid monomer (e.g., acrylic acid), about 23 to about 31 weight percent (e.g., about 27 weight percent) (meth)acrylamido alkyl or aryl sulfonate monomer (e.g., AMPS) and about 5 to about 12 weight percent (e.g., about 8.5 weight percent) third monomer (e.g., t-butyl acrylamide), for example, having a molecular weight ranging from about 4500 to about 5500 weight average molecular weight.

The polymeric dispersing agents useful in the compositions described herein can be prepared by methods of polymerization well known to those skilled in the art. For example, the first polymeric dispersing agents can be prepared by aqueous, solvent or emulsion polymerization. Methods for making the first polymeric dispersing agent are disclosed in U.S. Pat. No. 5,854,197. The second polymeric dispersing agent can be made, for example, by solution polymerization in water, optionally with an alcoholic cosolvent, for example, as described in U.S. Pat. No. 4,711,725, and in U.S. Pat. Nos. 4,314,004, 4,301,266, and 3,646,099, each of which is hereby incorporated herein by reference in its entirety. As the person of ordinary skill in the art will appreciate, polymeric materials that are copolymers including, as polymerized units, acidic monomers or vinyl alcohol monomers can be made initially from different monomers, then converted after polymerization to the desired monomeric units. For example, copolymers of maleic acid can be made by making a copolymer of maleic anhydride, then converting the anhydride to acid or salt form by addition of water and base. Similarly, as is familiar to the person of ordinary skill in the art, copolymers of vinyl alcohol can be made by making a copolymer of vinyl acetate, then converting the acetates to vinyl alcohol units by hydrolysis.

In certain embodiments of the compositions as described herein, the pymetrozine is present in the composition in an amount within the range of about 10 wt % to about 50 wt %, for example, within the range of about 10 wt % to about 30 wt %, or within the range of about 20 wt % to about 30 wt %. In certain embodiments of the compositions as described herein, the first polymeric dispersing agent and the second polymeric dispersing agent are present in the composition in a total amount within the range of about 5 wt % to about 15 wt %, or within the range of about 5 wt % to about 10 wt %. In certain embodiments of the compositions as described herein, the weight ratio of the of the first polymeric dispersing agent to the second polymeric dispersing agent is within the range of about 1:7 to about 1:2. For example, in one embodiment of the compositions as described herein the weight ratio of the of the first polymeric dispersing agent to the second polymeric dispersing agent is within the range of about 1:7 to about 1:3.

As the person of ordinary skill in the art will appreciate, the compositions described herein can include a variety of other ingredients. For example, in certain embodiments of the compositions as described herein, the composition further includes a wetting agent. The wetting agent can be provided, for example, in an amount up to about 5 wt %, e.g., within the range of about 1 wt % to about 5 wt %, or within the range of about 1 wt % to about 3 wt %. A variety of wetting agents can be used in the compositions as described herein; the person of ordinary skill in the art will select an appropriate agriculturally acceptable wetting agent for a particular formulation. For example, in certain embodiments, the wetting agent is selected from the group consisting of α-olefin sulfonates, sodium lignosulphonate, sodium dodecyl benzenesulfonate, sodium dodecyl sulfate, alkyl naphthalenesulfonic acid formaldehyde condensation products, ethoxylated and/or propoxylated copolymers, alkyldiphenyloxide disulfonate salts, alcohol alkoxylates, and alcohol alkoxylate sulfates. As the person of ordinary skill in the art will appreciate, a variety of surfactants can be suitable for use as wetting agents, as described, for example, in U.S. Pat. No. 4,931,439, which is hereby incorporated by reference in its entirety. Certain wetting agents are available under the trade names EXTRAVON, SYNPERONIC, ATERBANE and SILWET, ECOSURF, TERGITOL.

In certain embodiments of the compositions as described herein, the composition further includes a defoamer. For example, the defoamer can be present in the composition in an amount up to about 1 wt %, e.g., within the range of about 0.1 wt % to about 1 wt %. A variety of defoamers can be used in the compositions as described herein; the person of ordinary skill in the art will select an appropriate agriculturally acceptable defoamer for a particular formulation. For example, in certain embodiments, the defoamer is selected from the group consisting of silicone oil and other silicones, $C_{10-20}$ saturated fatty acids and $C_{8-10}$ fatty alcohols. One example of an appropriate defoamer is Dow Corning DK Q1-1247.

In certain embodiments of the compositions as described herein, the composition further includes a thickener. For example, the thickener can be present in the composition in an amount up to about 10 wt %, e.g., within the range of about 1 wt % to about 10 wt %. A variety of thickeners can be used in the compositions as described herein; the person of ordinary skill in the art will select an appropriate agriculturally acceptable thickener for a particular formulation. For example, in certain embodiments, the thickener is selected from the group consisting of xanthan gum, carboxymethylcellulose, hydroxyethylcellulose, cellulose methyl ether and polyvinyl alcohol. Other suitable thickeners include gum arabic, carrageenan, tragacanth gum, zanflow, pectin, guar gum, other methylated, carboxyalkylated or hydroxyalkylated products of cellulose or starch derivatives, such as hydroxymethyl cellulose, sorbitol, etc, polyacrylic salts, polymaleic salts, polyvinyl pyrrolidone and ethylene oxide adducts to pentaerythritol.

In certain embodiments of the compositions as described herein, the composition further includes an antifreeze agent. For example, the antifreeze agent can be present in the composition in an amount up to about 10 wt %, for example, within the range of about 1 wt % to about 10 wt %. A variety of antifreeze agents can be used in the compositions as described herein; the person of ordinary skill in the art will select an appropriate agriculturally acceptable antifreeze agent for a particular formulation. For example, in certain embodiments, the antifreeze agent is selected from the group consisting of glycols such as ethylene glycol and propylene glycol, glyceryl alcohol, and polyethylene glycol.

In certain embodiments of the compositions as described herein, the composition further includes water. As the person of ordinary skill in the art will appreciate, it can be desirable to include sufficient water to provide a substantially liquid composition. For example, in certain embodiments of the compositions as described herein, the composition includes water in an amount up to about 80 wt %. In certain such embodiments, the composition includes up to about 70 wt % water, or even up to about 65 wt % water. In certain embodiments of the compositions as described herein, the composition includes at least about 10 wt %, at least about 20 wt %, or even at least about 40 wt % water. In other embodiments, the composition is provided in the form of a wettable powder.

As the person of ordinary skill in the art will appreciate, various other adjuvants can be added into the compositions as described herein, for example in a total amount up to about 10 wt %, e.g., about 0.1 wt % to about 10 wt %. For example, in certain embodiments of the compositions as described herein, the composition further includes one or more of a penetrating agent, a pH adjusting agent, a stabilizer, and a biocide. The person of ordinary skill in the art will select appropriate agriculturally-acceptable adjuvants for a particular formulation. For example, the penetrating agent can be a silicone-based surfactant. Conventional penetrating agents are sold, for example, under the trade names SiSiB PC9273, SiSiB PC9277, RESPOND 30, AGRIBOND HF, BA35 and KY-1028. The person of ordinary skill in the art can use conventional inorganic and/or organic acids, bases and buffers to provide a desired pH to the composition. Examples of stabilizers suitable for use in the compositions described herein include, for example, BHA (butylated hydroxyanisole) and BHT (butylated hydroxytoluene). Examples of biocides suitable for use in the compositions described herein include, for example, KATHON™ brand materials.

One or more additional active ingredients can be included in the compositions described herein. Accordingly, in certain embodiments of the compositions as described herein, the composition further includes one or more additional active agents, for example, in an amount up to about 25 wt %, up to about 15 wt %, or up to about 10 wt %. As the person of ordinary skill in the art will appreciate, a wide variety of additional active ingredients can be used; preferably, the additional active ingredients do not affect the efficacy of pymetrozine. Examples of additional active agents include strobilurin fungicides such as Krexosim-methyl, pyridaben, imidacloprid, fenoxycarb, ethiprole, thiamethoxam, mobucin, nitenpyram, abamectin, buprofezin, thiacloprid, ethofenprox or acetanaprid.

In certain embodiments of the compositions as described herein, the composition includes the components listed in Table 1 below:

TABLE 1

| Component | Amount |
| --- | --- |
| pymetrozine | about 10 wt %-about 50 wt % (e.g., about 10 wt %-about 30 wt %) |
| first polymeric dispersing agent and second polymeric dispersing agent | about 5 wt %-about 15 wt % (total) (e.g., about 5 wt %-about 10 wt % total) |
| wetting agent | 0 wt %-about 15 wt % (e.g. about 5 wt % to about 15 wt %) |
| defoamer | 0 wt %-about 1 wt % (e.g., about 0.1 wt % to about 1 wt %) |
| thickener | 0 wt %-about 10 wt % (e.g., about 1 wt %-about 10 wt %) |
| antifreeze agent | 0 wt %-about 10 wt % (e.g., about 1 wt %-about 10 wt %) |
| other adjuvants | 0 wt %-about 10 wt % (e.g., about 0.1 wt %-about 10 wt %) |
| other active agents | 0 wt %-about 25 wt % (e.g., 0 wt %-15 wt %) |

The components of Table 1 can, for example, be provided as an aqueous suspension (i.e., with water forming the bulk of the remaining liquid).

As noted above, in certain embodiments the compositions as described herein can be provided with a variety of desirable properties. The person of ordinary skill in the art will, in view of the present disclosure, adjust the identities and amounts of various components to arrive at a desirable set of properties for a given use.

The compositions as described herein can be provided with a range of viscosities depending, for example, on the identities and amounts of pymetrozine, dispersing agents and thickener. Too high a viscosity can make the compositions difficult to measure, pour and dilute. For example, in certain embodiments of the compositions as described herein, the composition has a viscosity less than about 3000 mPa·s, or even less than about 2000 mPa·s at a shear rate of 20 s$^{-1}$. However, in many circumstances it can be desirable for a pymetrozine composition to be somewhat viscous, so that any particle settling that occurs would occur slowly. For example, in certain embodiments, the composition has a viscosity within the range of about 500 mPa·s to about 3000 mPa·s, or even within the range of about 1000 mPa·s to about 2000 mPa·s at a shear rate of 20 s$^{-1}$. As measured herein, viscosity is measured on a TA rheometer at room temperature.

In certain embodiments, the compositions as described herein are relatively low-foaming, which can be desirable in the measuring, dilution and application processes. Foaming characteristics will depend, for example, on the amounts of pymetrozine, dispersing agents, defoamer. In certain embodiments of the compositions as described herein, the composition has a persistent foam volume no greater than about 30 mL, or even no greater than about 20 mL. Persistent foaming volume is evaluated according to CIPAC MT 47, which is hereby incorporated herein by reference in its entirety. To determine the persistent foam volume, a glass-stoppered 250 mL graduated cylinder having a distance between 0 and 250 mL marks of 20-21.5 cm and a distance between the 250 mL mark and the bottom of the stopper of 4-6 cm is used. Water (~180 mL) and sample (1 g) is measured into the graduated cylinder, and then the cylinder is topped up with water so that the distance between the water level and the bottom of the ground glass joint is 9.0±0.1 cm. The cylinder is stoppered and inverted 30 times, after which the stoppered cylinder is placed upright on a flat surface and a stopwatch is started. The volume of foam produced and remaining after one minute is measured.

Advantageously, in certain embodiments the compositions as described herein can provide a high degree of suspensibility. Suspension rate is used as a measure of the ability of a diluted pymetrozine composition to maintain the pymetrozine particulates in suspension, which can be desirable for uniform application of pymetrozine in an agricultural setting. In certain embodiments of the compositions as described herein, the composition has a suspension rate of at least about 90%, or even of at least about 95%. Suspension rate is evaluated according to CIPAC MT161 and MT 184, each of which is hereby incorporated herein by reference in its entirety. A pymetrozine composition sample (0.5±0.0002 g) is added to 100 mL water in a 250 mL graduated cylinder at 30±0.2° C. The graduated cylinder is topped up with water to the 250 mL mark. The cylinder is inverted 30 times in the span of one minute, then allowed to stand at 30±0.2° C. for 30 minutes. The top 9/10 of the liquid is removed (e.g., via pipette), and the bottom 1/10 of the liquid (i.e., about 25 mL) is allowed to evaporate and the residue is weighed. Suspension rate is calculated according to the formula below, in which M1 is the weight of the active ingredient in the sample, and M2 is the weight of the active ingredient remaining in the residue:

$$S(\%) = \frac{(M1 - M2)}{M1} \times \frac{10}{9} \times 100$$

To prepare a standard hard water, anhydrous calcium chloride (0.304 g) and magnesium chloride hexahydrate (0.139 g) are dissolved in deionized water and diluted to scale in a 1000 mL volumetric flask.

In certain embodiments of the compositions as described herein, the composition has a dilute pH value within the range of about 4.0 to about 9.0. In certain embodiments, the composition has a dilute pH value within the range of about 6.5 to about 9.0, for example, within the range from about 7.0 to about 9.0. In other embodiments, the composition has a dilute pH value within the range of about 4.0 to about 7.5, for example, within the range from about 4.0 to about 7.0. Dilute pH values are determined according to CIPAC MT 75.3, which is hereby incorporated herein by reference in its entirety. A concentrated composition (1 g) is diluted with 100 mL deionized water, and the pH measured with a pH meter.

The compositions described herein can be made to be storage stable. For example, in certain embodiments of the compositions described herein, the composition has, after storage at 54° C. for 14 days, a mean particle size within the range about 0.1 to about 10 μm, for example, within the range of about 0.5 to about 5 μm or within the range of about 0.5 to about 5 μm; a median particle size within the range of about 0.1 to about 10 μm, for example, within the range of about 0.5 to about 5 μm or within the range of about 0.5 to about 5 μm; or a mean particle size and a median particle size each within the range of about 0.1 to about 10 μm, for example, within the range of about 0.5 to about 5 μm or within the range of about 0.5 to about 5 μm. In certain embodiments of the compositions as described herein, the composition has, after storage at 54° C. for 14 days, a $D_{90}$ no greater than about 10 μm, no greater than about 5 μm. In certain embodiments of the compositions described herein, the composition has, after storage at 54° C. for 14 days, the composition has a viscosity less than about 3000 mPa·s, or even less than about 2000 mPa·s at a shear rate of 20 $s^{-1}$ In certain embodiments of the compositions described herein, the composition has, after storage at 54° C. for 14 days, a viscosity within the range of about 500 mPa·s to about 3000 mPa·s, or even within the range of about 1000 mPa·s to about 2000 mPa·s at a shear rate of 20 $s^{-1}$.

In certain embodiments of the compositions described herein, the composition has, after storage at 0° C. for 7 days, a mean particle size within the range about 0.1 to about 10 μm, for example, within the range of about 0.5 to about 5 μm or within the range of about 0.5 to about 5 μm; a median particle size within the range of about 0.1 to about 10 μm, for example, within the range of about 0.5 to about 5 μm or within the range of about 0.5 to about 5 μm; or a mean particle size and a median particle size each within the range of about 0.1 to about 10 μm, for example, within the range of about 0.5 to about 5 μm or within the range of about 0.5 to about 5 μm. In certain embodiments of the compositions as described herein, the composition has, after storage at 0° C. for 7 days, a $D_{90}$ no greater than about 10 μm, no greater than about 5 μm. In certain embodiments of the compositions described herein, the composition has, after storage at 0° C. for 7 days, the composition has a viscosity less than about 3000 mPa·s, or even less than about 2000 mPa·s at a shear rate of 20 $s^{-1}$ In certain embodiments of the compositions described herein, the composition has, after storage at 2° C. for 7 days, a viscosity within the range of about 500 mPa·s to about 3000 mPa·s, or even within the range of about 1000 mPa·s to about 2000 mPa·s at a shear rate of 20 $s^{-1}$.

Another embodiment of the invention is a method for making a composition as described herein, the method including providing a first polymeric dispersing agent as described herein;

providing a second polymeric dispersing agent as described herein;

mixing the first polymeric dispersing agent and the second polymeric dispersing agent and water with particulate pymetrozine with high-speed shearing; and grinding the resulting mixture.

In certain such embodiments, the water is mixed with the first polymeric dispersing agent and the second polymeric dispersing agent before being mixed with the particulate pymetrozine. Other components can be mixed with the water and the dispersing agents before combination with the particulate pymetrozine. For example, in certain embodiments, one or more of a wetting agent and a defoamer can be mixed with the water before combination with the particulate pymetrozine.

The grinding can be performed under conditions sufficient to provide the desired pymetrozine particle size, as would be recognized by the person of ordinary skill in the art. For example, the grinding can be performed using grinding media such as grinding beads, e.g., in a sand miller. After the grinding step, the mixture can be filtered to remove grinding media and any other larger particulate matter.

Additional components of the formulation can be added at any convenient time. For example, the ground and filtered composition can be combined with one or more of a thickener, an anti-freeze agent or a biocide as described above, along with any additional water necessary to provide the desired properties to the overall composition. High speed shearing can be used to provide the final concentrated pymetrozine composition.

One embodiment of a method form making the compositions as described herein is shown in flowchart form in the FIGURE. First, the first and second dispersing agents along with any wetting agent are dissolved in water. Defoamer is then added. Solid pymetrozine is added, and the mixture is mixed with high-speed shearing to form a slurry. The slurry is milled in a sand miller with grinding beads for two hours, after which time the mixture is filtered with a 100 mesh filter to remove the grinding beads and any larger particles of pymetrozine. Other adjuvants, e.g., thickener, antifreeze agent, biocide, can be added at this time, and mixed with high-speed shearing.

In another aspect, the disclosure provides a method for reducing insect populations on a plant, the method comprising diluting a composition as described herein with water to provide a diluted pymetrozine composition; and contacting the plant with the diluted pymetrozine concentration.

Unless clearly excluded by the context, all embodiments disclosed for one aspect of the invention can be combined with embodiments disclosed for other aspects of the invention, in any suitable combination.

EXAMPLES

The following examples are presented to illustrate the embodiments of the present invention and are not intended to constitute a limitation on their scope, which is defined in the appended claims.

Three pymetrozine concentrate formulations were prepared as described above with respect to the FIGURE. Table 2 provides the compositions of Examples 1, 2 and 3.

TABLE 2

| ingredient | Example 1 | Example 2 | Example 3 |
| --- | --- | --- | --- |
| Pymetrozine powder | 25% | 25% | 16% |
| Ethofenprox | | | 5% |
| sodium dodecyl benzene sulfonate | 2% | 2% | 2% |
| Second polymeric dispersing agent | 6% | 8% | 6% |
| First polymeric dispersing agent | 2% | 1% | 2% |
| Silicone defoamer (DK1247) | 0.1% | 0.1% | 0.1% |
| Xanthan (2%) | 5% | 5% | 5% |
| propylene glycol | 5% | 5% | 5% |
| biocide | 0.1% | 0.1% | 0.1% |
| water | Add to 100% | Add to 100% | Add to 100% |

In Examples 1, 2 and 3, the first polymeric dispersing agent is a copolymer of 51 percent maleic acid (provided as the sodium salt) and 49 weight percent diisobutylene; and the second polymeric dispersing agent is a copolymer of 64.5 weight percent acrylic acid; 27 weight percent AMPS; and 8.5 weight percent t-butyl acrylamide.

The physical and chemical characteristics of the Examples 1 and 3 formulations were determined as described above. Results are described below in Tables 3 and 4. The storage properties of the Example 2 composition are also described below.

TABLE 3

Example 1

| | | Room temperature | Storage at 54° C. for 14 days | Storage at 2° C. for 7 days |
| --- | --- | --- | --- | --- |
| Appearance | | Free-flowing | No water extraction, no deposit, free-flowing | No water extraction, no deposit, free-flowing |
| pH(1%) at 20° C. | | 5.35 | 5.30 | 5.27 |
| Viscosity (mPa · s) at 20 s$^{-1}$ shear rate | | 1850 | 1500 | 1600 |
| Suspension rate (%) | | 97.4 | 97.2 | 97.5 |
| Persistent foam volume (mL) | | 15 | 15 | 20 |
| Particle size (μm) | Mean | 0.894 | 1.299 | 1.352 |
| | Medium | 0.531 | 0.907 | 0.848 |
| | $D_{10}$ | 0.153 | 0.249 | 0.222 |
| | $D_{50}$ | 0.531 | 0.907 | 0.848 |
| | $D_{90}$ | 1.934 | 2.842 | 3.199 |
| Evaluation results | Active content | qualified | qualified | qualified |
| | pH | qualified | qualified | qualified |
| | Viscosity | qualified | qualified | qualified |
| | Suspensibility | qualified | qualified | qualified |
| | Particle size | qualified | qualified | qualified |

Example 2

The prepared sample caked after heat storage at 54° C. for 14 days, indicating that the mixing ratio of the first polymeric dispersing agent to the second polymeric dispersing agent can be important for formulation flowability upon storage.

TABLE 4

Example 3

| | | Room temperature | Storage at 54° C. for 14 days | Storage at 0° C. for 7 days |
| --- | --- | --- | --- | --- |
| Appearance | | Free-flowing | No water extraction, no deposit, free-flowing | No water extraction, no deposit, free-flowing |
| Suspension rate (%) | | 93.7 | 92.1 | 93.0 |
| pH(1%) at 20° C. | | 5.33 | 5.41 | 5.35 |
| Persistent foam volume (mL) | | 10 | 10 | 10 |
| Particle size (μm) | Mean | 2.711 | 3.163 | 2.256 |
| | D10 | 1.440 | 1.438 | 0.377 |
| | D50 | 2.536 | 2.626 | 2.045 |
| | D90 | 4.239 | 5.161 | 4.319 |
| Evaluation results | | qualified | qualified | qualified |

It is understood that the examples and embodiments described herein are for illustrative purposes only. Unless clearly excluded by the context, all embodiments disclosed for one aspect of the invention can be combined with embodiments disclosed for other aspects of the invention, in any suitable combination. It will be apparent to those skilled in the art that various modifications and variations can be made to the present invention without departing from the scope of the invention. Thus, it is intended that the present invention cover the modifications and variations of this invention provided they come within the scope of the appended claims and their equivalents. All publications, patents, and patent applications cited herein are hereby incorporated herein by reference for all purposes.

What is claimed is:

1. A composition comprising
   pymetrozine;
   a first polymeric dispersing agent, the first polymeric dispersing agent being a copolymer comprising as polymerized units (a) from about 20 to about 90 weight percent, based on total polymer weight, of a maleic acid monomer selected from one or more of maleic acid, maleic anhydride and water-soluble salts thereof, and (b) from about 10 to about 80 weight percent, based on total polymer weight, of a hydrophobic monomer selected from one or more of alkenes, dienes, alkynes and aromatic compounds, each containing from 4 to 20 carbon atoms; and
   a second polymeric dispersing agent, the second polymeric dispersing agent being a copolymer comprising as polymerized units (a) from about 10 to about 84 weight percent, based on total polymer weight, of a (meth)acrylic acid monomer selected from one or more of (meth)acrylic acid and salts thereof, (b) from about 11 to about 40 weight percent, based on total polymer weight, of a (meth)acrylamido alkyl or aryl sulfonate monomer; and (c) from about 5 to about 50 weight percent based on total polymer weight, of a third monomer selected from one or more of vinylic compounds, (meth)acrylic esters, vinyl acetate, and substituted (meth)acrylamides.

2. The composition according to claim 1, wherein
   the pymetrozine is present in the composition in an amount within the range of about 10 wt % to about 50 wt %; and
   the first polymeric dispersing agent and the second polymeric dispersing agent are present in a total amount within the range of about 5 wt % to about 15 wt %, wherein the weight ratio of the first polymeric dispersing agent to the second polymeric dispersing agent is within the range of about 1:7 to about 1:3.

3. The composition according to claim 1, wherein the first polymeric dispersing agent comprises, as polymerized units, from about 30 to about 60 weight percent, based on total polymer weight, of the maleic acid monomer, and from about 40 to about 70 weight percent, based on total polymer weight, of the hydrophobic monomer selected from one or more of alkenes, dienes, alkynes and aromatic compounds.

4. The composition according to claim 1, wherein the maleic acid monomer is maleic acid.

5. The composition according to claim 1, wherein the hydrophobic monomer is selected from one or more of isobutylene, diisobutylene, styrene, decene, limonene, linalool and eicosene.

6. The composition according to claim 1, wherein the hydrophobic monomer is diisobutylene.

7. The composition according to claim 1, wherein the first polymeric dispersing agent includes no monomers other than the (meth)acrylic acid monomer and the hydrophobic monomer.

8. The composition according to claim 1, wherein the first polymeric dispersing agent comprises, as polymerized units, about 46 to about 56 weight percent maleic acid monomer and about 44 to about 54 weight percent diisobutylene.

9. The composition according to claim 1, wherein the first polymeric dispersing agent has a weight-average molecular weight within the range of about 1 kDa to about 20 kDa.

10. The composition according to claim 1, wherein the second polymeric dispersing agent is a copolymer comprising as polymerized units, from about 30 to about 84 weight percent of the (meth)acrylic acid monomer; from about 11 to about 40 weight percent of the (meth)acrylamido alkyl or aryl sulfonate monomer; and about 5 to about 30 weight percent of the third monomer.

11. The composition according to claim 1, wherein the second polymeric dispersing agent is a copolymer comprising, as polymerized units, about 61 to about 68 weight percent (meth)acrylic acid monomer, about 23 to about 31 weight percent (meth)acrylamido alkyl or aryl sulfonate monomer and about 5 to about 12 weight percent by weight of a (meth)acrylic ester, vinyl acetate or alkyl-substituted (meth)acrylamide.

12. The composition according to claim 1, wherein the second polymeric dispersing agent has a weight-average molecular weight within the range of about 3 kDa to about 25 kDa.

13. The composition according to claim 1, further comprising, in any combination, one or more of
 (a) a wetting agent in an amount within the range of about 1 wt % to about 5 wt %;
 (b) a defoamer in an amount within the range of about 0.1 wt % to about 1 wt %;
 (c) a thickener in an amount within the range of about 1 wt % to about 10 wt %; and
 (d) an antifreeze agent in an amount within the range of about 1 wt % to about 10 wt %.

14. The composition according to claim 1, further comprising water in an amount up to about 80 wt %.

15. The composition according to claim 14, having a viscosity less than about 2000 mPa·s at a shear rate of 20 s$^{-1}$ and a persistent foam volume no greater than about 20 mL.

* * * * *